(12) United States Patent
Guerrera et al.

(10) Patent No.: US 12,714,530 B2
(45) Date of Patent: Aug. 25, 2026

(54) ROBOTIC SURGICAL SYSTEMS AND ROBOTIC ARM CARTS THEREOF

(71) Applicant: Covidien LP, Mansfield, MA (US)

(72) Inventors: Joseph M. Guerrera, Watertown, CT (US); Shane Reardon, Branford, CT (US); Noah N. Yang, New Haven, CT (US)

(73) Assignee: Covidien LP, Mansfield, MA (US)

( * ) Notice: Subject to any disclaimer, the term of this patent is extended or adjusted under 35 U.S.C. 154(b) by 296 days.

(21) Appl. No.: 18/289,938

(22) PCT Filed: Jun. 28, 2022

(86) PCT No.: PCT/IB2022/056016
§ 371 (c)(1),
(2) Date: Nov. 8, 2023

(87) PCT Pub. No.: WO2023/275758
PCT Pub. Date: Jan. 5, 2023

(65) Prior Publication Data

US 2024/0261052 A1 Aug. 8, 2024

Related U.S. Application Data

(60) Provisional application No. 63/217,866, filed on Jul. 2, 2021.

(51) Int. Cl.
*A61B 50/13* (2016.01)
*A61B 34/30* (2016.01)

(52) U.S. Cl.
CPC .............. *A61B 50/13* (2016.02); *A61B 34/30* (2016.02)

(58) Field of Classification Search
CPC ......... A61B 34/30; A61B 34/37; A61B 90/50; A61B 2090/508; B60B 2200/26; B60B 33/021; B60B 33/026
See application file for complete search history.

(56) References Cited

U.S. PATENT DOCUMENTS 5,237,815 A * 8/1993 McArthur ................. F02N 7/00 60/627
5,624,352 A 4/1997 Smale
2011/0120815 A1* 5/2011 Frolik ................. B60B 33/0081 188/1.12
2018/0132884 A1* 5/2018 Denzinger ......... A61B 17/2804
(Continued)

FOREIGN PATENT DOCUMENTS

CN 209826974 U 12/2019
EP 1581417 B1 11/2006
(Continued)

OTHER PUBLICATIONS

Machine translation of CN 209826974 U (Year: 2019).*
(Continued)

*Primary Examiner* — Farhana Pervin
(74) *Attorney, Agent, or Firm* — Carter, DeLuca & Farrell, LLP

(57) ABSTRACT

A surgical cart for supporting a robotic arm includes a base, a plurality of casters coupled to the base, and a secondary braking mechanism that prevents the casters from being manually moved out of a locked state until a surgical instrument is at a safe distance from an operative site within a patient.

20 Claims, 11 Drawing Sheets

(56) References Cited

U.S. PATENT DOCUMENTS

| | | | | |
|---|---|---|---|---|
| 2020/0352664 | A1* | 11/2020 | King | G16H 30/40 |
| 2022/0151713 | A1* | 5/2022 | Kapadia | B60B 33/021 |

FOREIGN PATENT DOCUMENTS

| | | | |
|---|---|---|---|
| EP | 2555929 | B1 | 11/2017 |
| WO | 2018052796 | A1 | 3/2018 |
| WO | 2019203999 | A1 | 10/2019 |

OTHER PUBLICATIONS

International Search Report and Written Opinion of the International Searching Authority issued in corresponding application PCT/IB2022/056016 mailed Sep. 21, 2022 (12 pages).

* cited by examiner

ROBOTIC SURGICAL SYSTEMS AND ROBOTIC ARM CARTS THEREOF

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within the patient's body.

Some robotic surgical systems employ a cart to support the robotic arm and allow a clinician to move the robotic arm to different locations within the operating room. While performing a surgical procedure, it would be desirable for the cart to be held in a stationary position.

SUMMARY

In accordance with an aspect of the disclosure, surgical cart for supporting a robotic arm is provided and includes a base, a caster coupled to the base, a brake pedal operably coupled to the base, and a latching solenoid coupled to the base adjacent the brake pedal. The brake pedal is configured to move between a first position and a second position. In the first position, the caster is free to roll, and in the second position the caster is prevented from rolling. The latching solenoid has a plunger configured to move between a first position and a second position. When the plunger is in the first position, the brake pedal is free to move between the first and second positions, and when the plunger is in the second position, the brake pedal is prevented from moving from the second position to the first position.

In aspects, the latching solenoid may be configured to automatically move the plunger from the first position to the second position in response to the brake pedal moving to the second position.

In aspects, the latching solenoid may be configured to automatically move the plunger from the second position to the first position upon receiving a communication that a surgical instrument is detached from the surgical robotic arm or the surgical instrument is removed from a patient.

In aspects, the surgical cart may further include a processor in communication with the latching solenoid and configured to cause the plunger to move between the first and second positions.

In aspects, the latching solenoid may be configured to automatically move the plunger from the first position to the second position upon both of the following occurring: the brake pedal is moved to the second position; and the latching solenoid receives a communication that a surgical instrument is attached to the robotic arm or the surgical instrument is within a patient.

In aspects, the surgical cart may further include a manual control knob attached to the plunger such that the plunger is manually movable from the second position to the first position.

In aspects, the surgical cart may further include a cover detachably coupled to the base and configured to conceal the manual control knob.

In accordance with another aspect of the disclosure, a surgical robotic assembly is provided and includes a surgical robotic arm configured to support a surgical instrument, a processor in communication with the surgical robotic arm, and a surgical cart. The surgical cart includes cart base, a support column extending vertically from the cart base and configured to support the surgical robotic arm, a caster coupled to the base, a brake pedal operably coupled to the base, and a latching solenoid coupled to the base adjacent the brake pedal. The brake pedal is configured to move between a first position, in which the caster is unlocked, and a second position, in which the caster is locked. The latching solenoid is in communication with the processor and is configured to, in response to a command from the processor, move a plunger between a first position and a second position. When the plunger is in the first position, the plunger does not prevent the brake pedal from moving from the second position to the first position. When the plunger is in the second position, the plunger prevents the brake pedal from moving from the second position to the first position.

In aspects, the surgical cart may further include a sensor assembly configured to determine whether the brake pedal is in the first or second positions.

In aspects, the sensor assembly may be configured to communicate to the processor the position of the brake pedal.

In aspects, the surgical robotic arm may include a sensor configured to determine whether the surgical instrument is attached thereto or whether the surgical instrument is within a patient. The processor may be configured to move the plunger from the first position to the second position upon both of the following occurring: the brake pedal is moved to the second position; and the sensor of the surgical robotic arm determines that the surgical instrument is attached to the surgical robotic arm or the surgical instrument is within a patient.

In aspects, the processor may be configured to cause the latching solenoid to move the plunger from the second position to the first position upon receiving a communication from the sensor of the surgical robotic arm that the surgical instrument is detached from the surgical robotic arm or the surgical instrument is removed from the patient.

In accordance with further aspects of the disclosure, a surgical cart for supporting a robotic arm is provided and includes a base, a caster coupled to the base, a brake pedal operably coupled to the caster, a latching solenoid coupled to the base, a manual control knob, and a cover. The brake pedal is configured to move between a first position, in which the caster is unlocked, and a second position, in which the caster is locked. The latching solenoid is configured to move a plunger between a first position and a second position. When the plunger is in the first position, the plunger does not prevent the brake pedal from moving from the second position to the first position, and when the plunger is in the second position, the plunger prevents the brake pedal from moving from the second position to the first position. The manual control knob is attached to the plunger such that the plunger is manually movable from the second position to the first position. The cover is detachably coupled to the base and configured to conceal the manual control knob.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
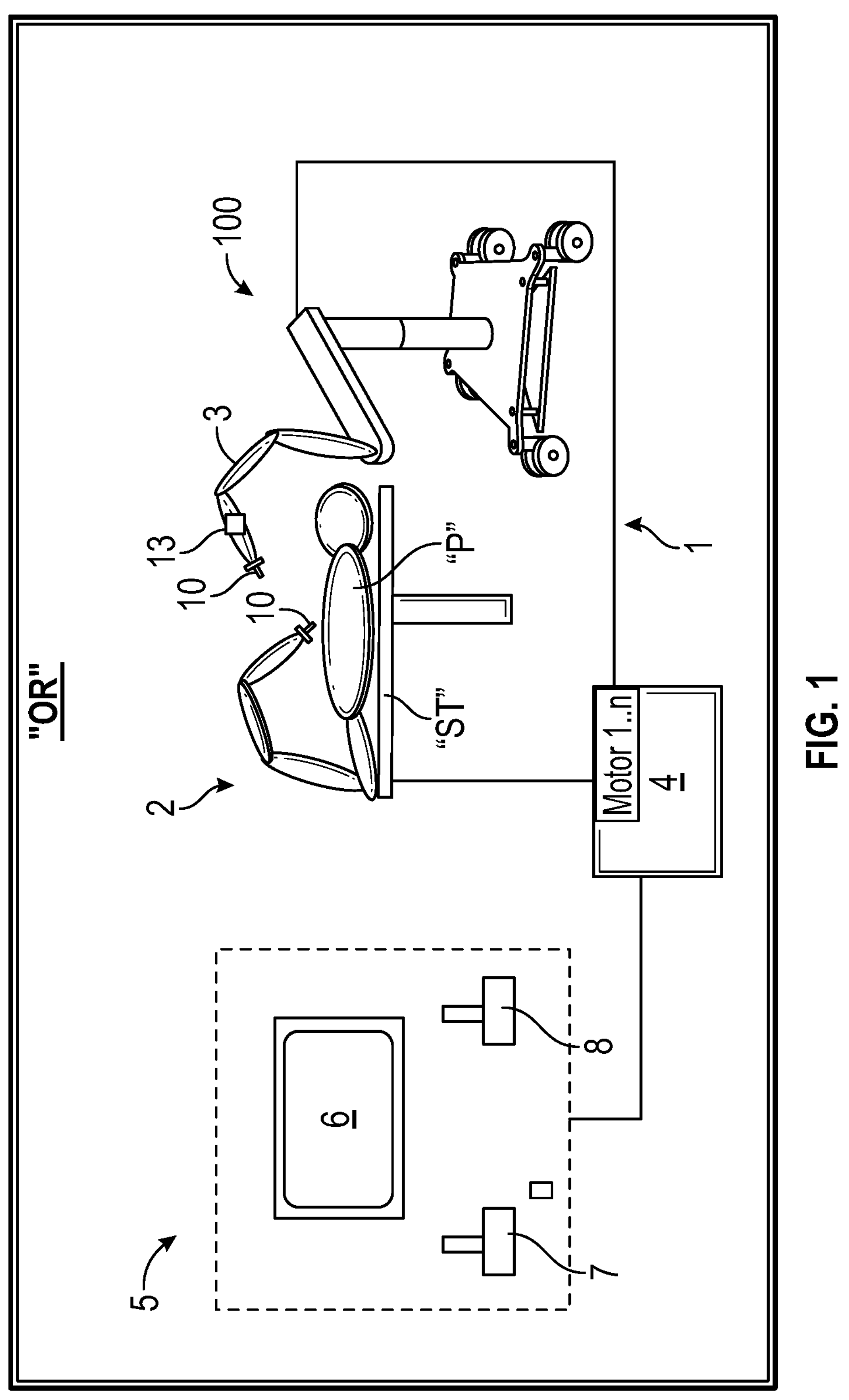
FIG. 1 is a schematic illustration of a robotic surgical system including a surgical cart in accordance with the present disclosure.

Embodiments of the presently disclosed robotic surgical systems including various embodiments of a robotic arm cart and methods of use thereof are described in detail with reference to the drawings, in which like reference numerals designate identical or corresponding elements in each of the several views. As used herein the term "distal" refers to that portion of the robotic surgical system or component thereof, that is closer to the patient, while the term "proximal" refers to that portion of the robotic surgical system or component thereof, that is farther from the patient.

As will be described in detail below, provided are embodiments of a surgical cart for supporting a robotic arm and for facilitating movement of the robotic arm around an operating room. The cart includes a base equipped with wheels, a support column extending vertically from the base, and a braking system that includes a series of interconnected linkages allowing for the selective locking and unlocking of the wheels of the cart.

Referring initially to FIG. 1, a surgical system, such as, for example, a robotic surgical system 1 is shown. In embodiments, robotic surgical system 1 is located in an operating room "OR." Robotic surgical system 1 generally includes a plurality of surgical robotic arms 2, 3 having a surgical instrument, such as, for example, an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), e.g., a clinician, is able to telemanipulate robotic arms 2, 3 in a first operating mode, as known in principle to a person skilled in the art. Each of the robotic arms 2, 3 may be composed of a plurality of members, which are connected through joints.

Robotic arms 2, 3 may be driven by electric drives (not shown) that are connected to control device 4. Control device 4 (e.g., a computer) is set up to activate the drives, in particular by means of a computer program, in such a way that robotic arms 2, 3 and thus electromechanical instrument 10 (including the electromechanical end effector (not shown)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more or less than two robotic arms 2, 3, the additional robotic arms likewise being connected to control device 4 and being telemanipulatable by means of operating console 5. A surgical instrument, for example, electromechanical instrument 10 (including the electromechanical end effector), may also be attached to the additional robotic arm.

Figure 2:
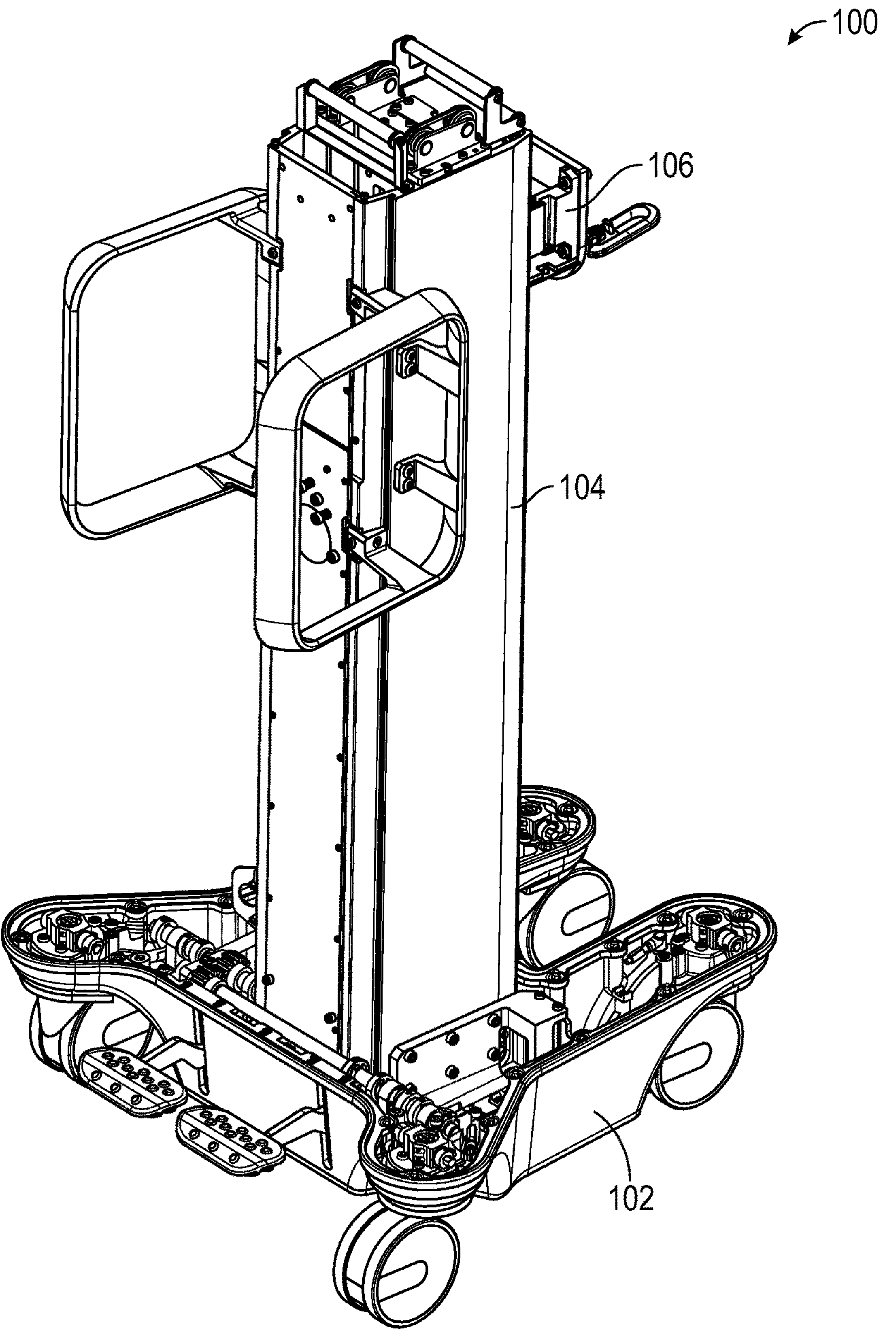
FIG. 2 is a perspective view of one embodiment of a surgical cart of the robotic surgical system of FIG. 1.

The robotic arms, such as for example, robotic arm 3, is supported on a surgical cart 100 (FIG. 2). The surgical cart 100 may incorporate the control device 4. In embodiments, the robotic arms, such as for example, robotic arm 2 may be coupled to the surgical table "ST."

With reference to FIG. 2, one exemplary embodiment of a surgical cart of robotic surgical system 1, configured for use in accordance with the present disclosure, is shown generally using reference numeral 100. The surgical cart 100 is configured to move robotic arm 3 (FIG. 1) to a selected position within operating room "OR" (FIG. 1) and to provide height adjustment of the robotic arm 3. The surgical cart 100 generally includes a cart base 102, a support column 104 extending vertically (i.e., perpendicularly) from the cart base 102, and a carriage or slider 106 slidably supported on the column 104 and configured for supporting the robotic arm 3 thereon.

With reference to FIGS. 2-5, the cart base 102 of the surgical cart 100 is fixed to a first end of the support column 104 and includes four casters 103*a*, 103*b*, 103*c*, 103*d*. In some embodiments, the cart base 102 may include more or less than four casters. The cart base 102 further includes two foot pedals 105*a*, 105*b* coupled to the casters 103*a*-103*d* via a braking mechanism 110 that functions to selectively unlock and lock the casters 103*a*-103*d* via actuation of the foot pedals 105*a*, 105*b*, respectively, as will be described in detail herein.

The braking mechanism 110 generally includes first and second rods 112, 114, first and second linkages 124, 134 coupled to the first rod 112, and first and second arms 148, 160 coupled to the second rod 114, each supported in the base 102. The first pedal 105*a* (e.g., a foot pedal) is non-rotationally coupled to the first rod 112, such that a depression of the first pedal 105*a* causes the first rod 112 to rotate in a first direction, indicated by arrow "A" in FIG. 5.

The second pedal **105*b* (e.g., a foot pedal) is non-rotationally coupled to the second rod 114, such that a depression of the second pedal 105*b* causes the second rod 114 to likewise rotate in the first direction. The first and second rods 112, 114 are parallel to one another and are operably coupled to one another via corresponding couplers, such as, for example, spur gears 116, 118. In this way, the first and second rods 112, 114 rotate in opposite directions from one another. For example, if the first pedal 105*a* is depressed, the first rod 112 rotates in the first direction driving a rotation of the second rod 114 in a second, opposing direction, indicated by arrow "B" in FIG. 5**.

Figure 3:
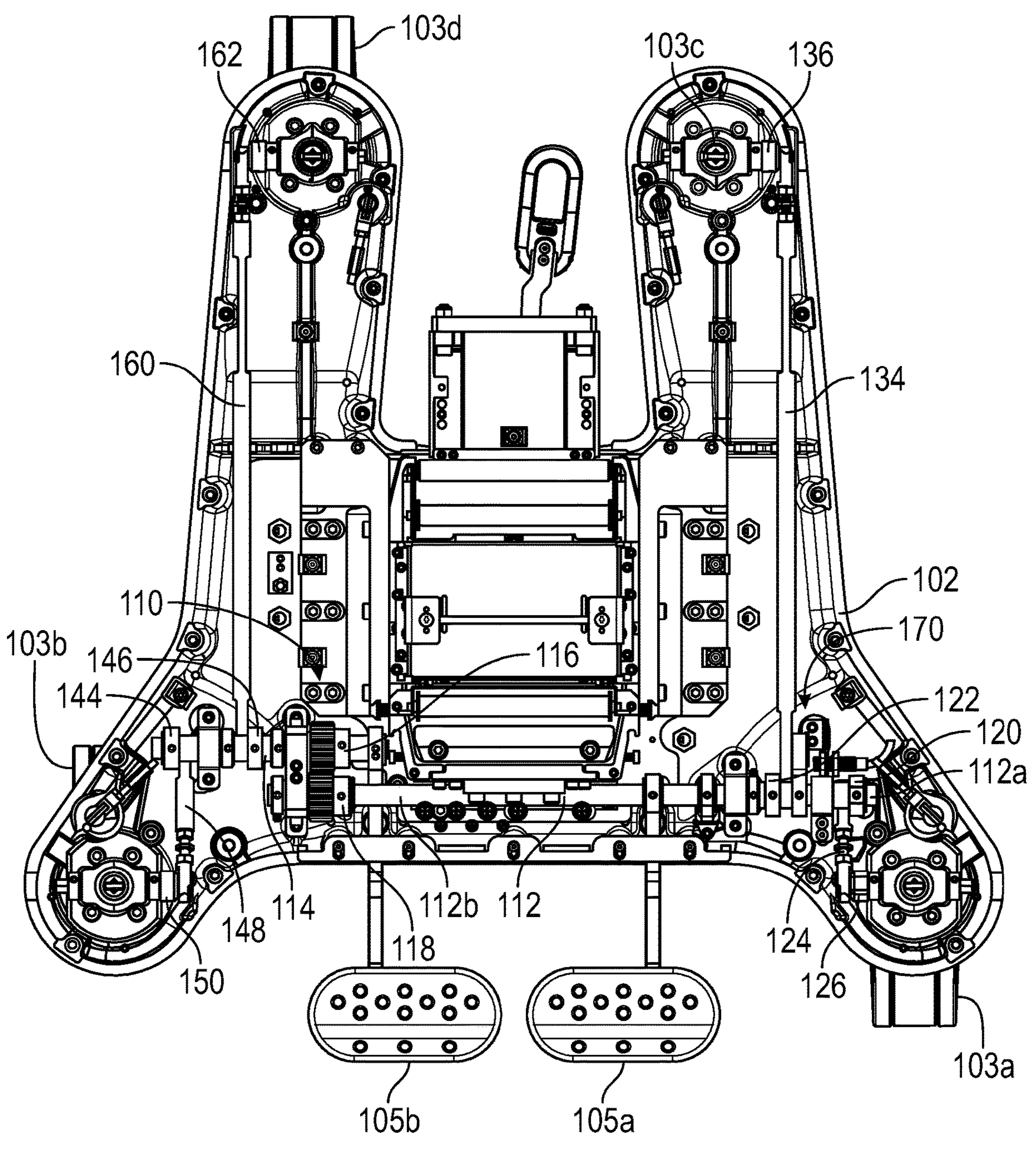
FIG. 3 is a top view, with a top cover removed, of the surgical cart of FIG. 2.
Figure 4:
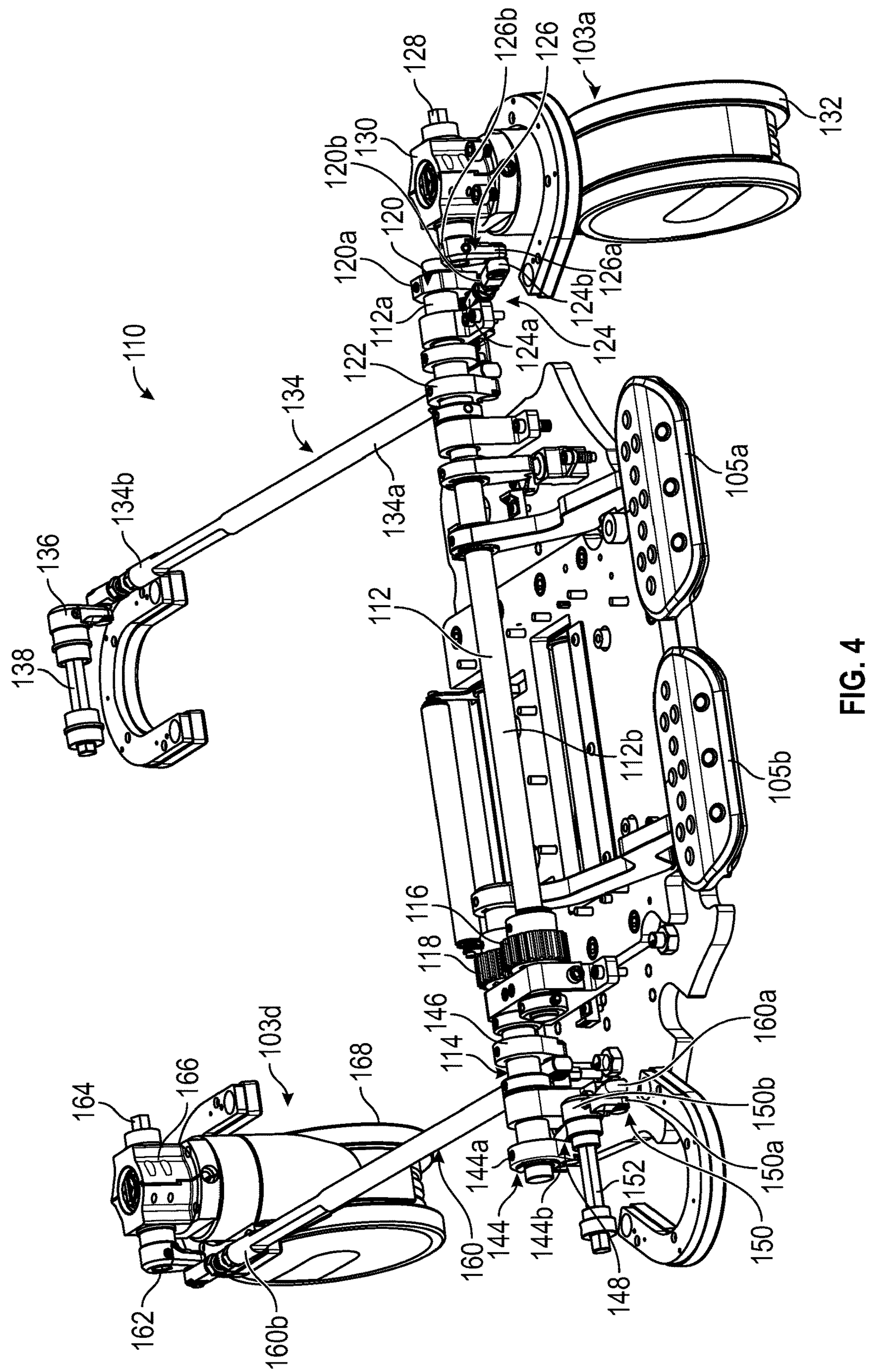
FIG. 4 is a rear, perspective view, with parts removed, of the surgical cart of FIG. 2.
Figure 5:
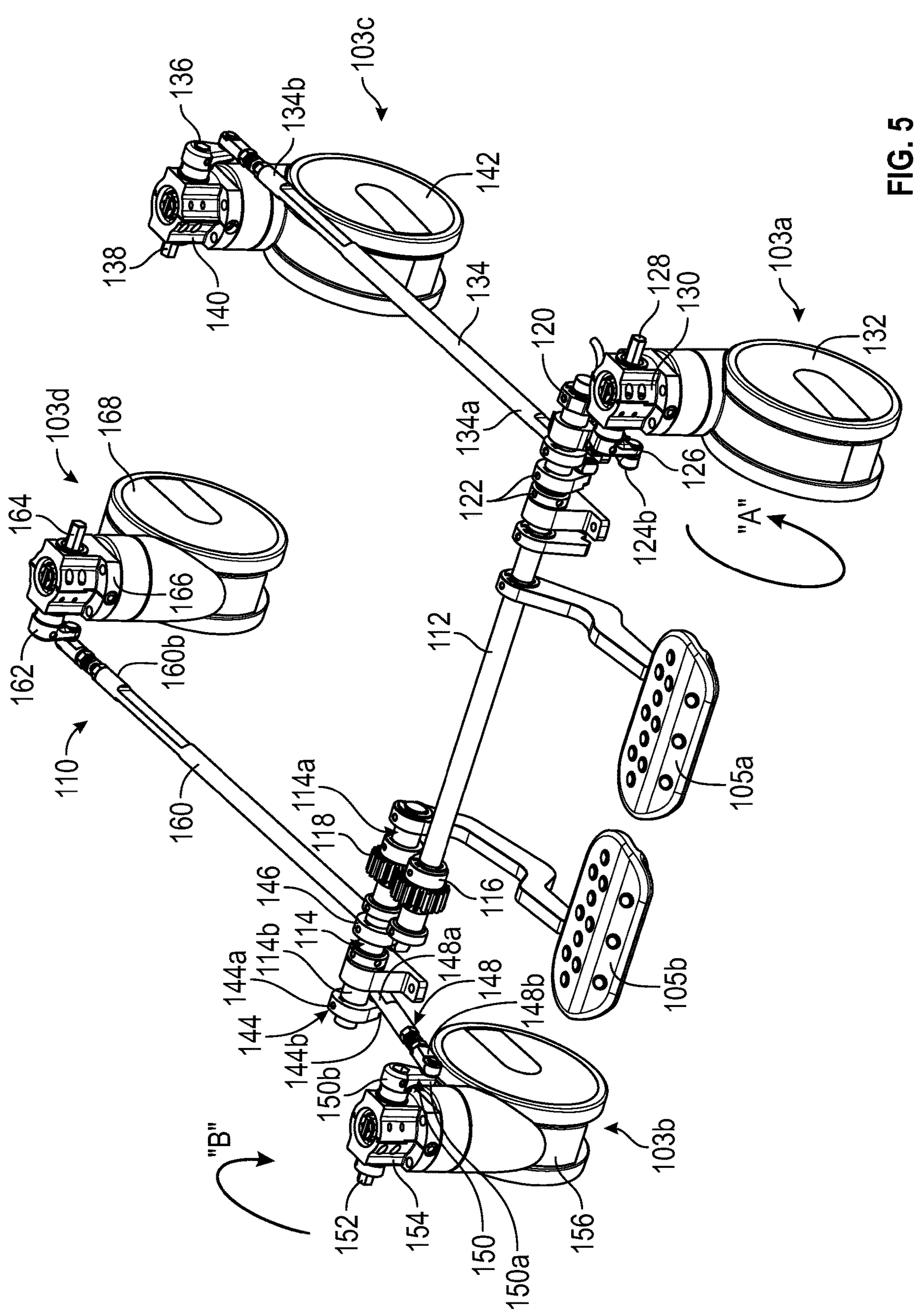
FIG. 5 is another rear, perspective view, with parts removed, of the surgical cart shown in FIG. 2.
Figure 6:
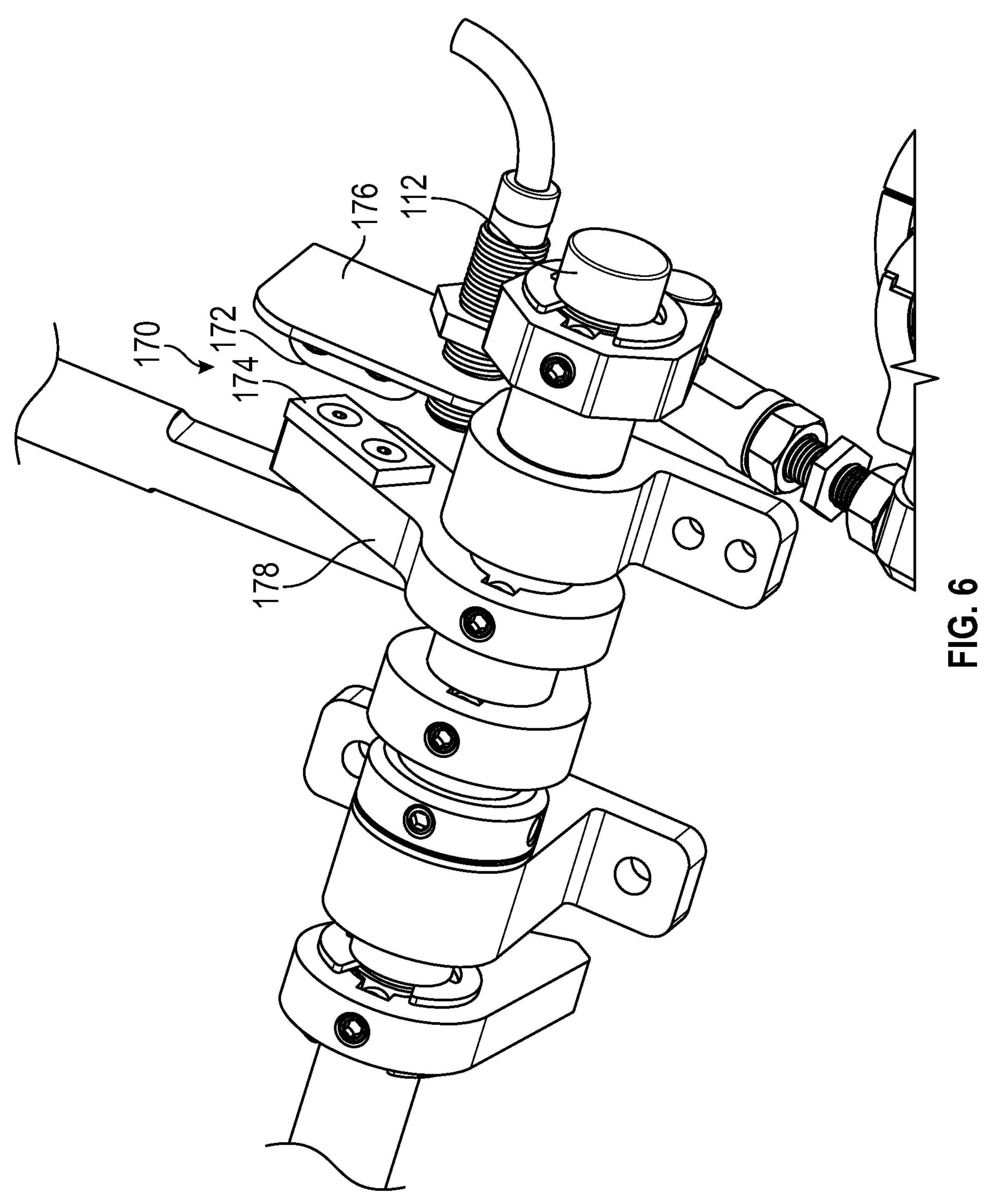
FIG. 6 is an enlarged view of a sensor assembly of the surgical cart of FIG. 2.
Figure 7:
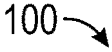
FIG. 7 is a side, perspective view illustrating a secondary braking mechanism coupled to the surgical cart of FIG. 2.
Figure 7:
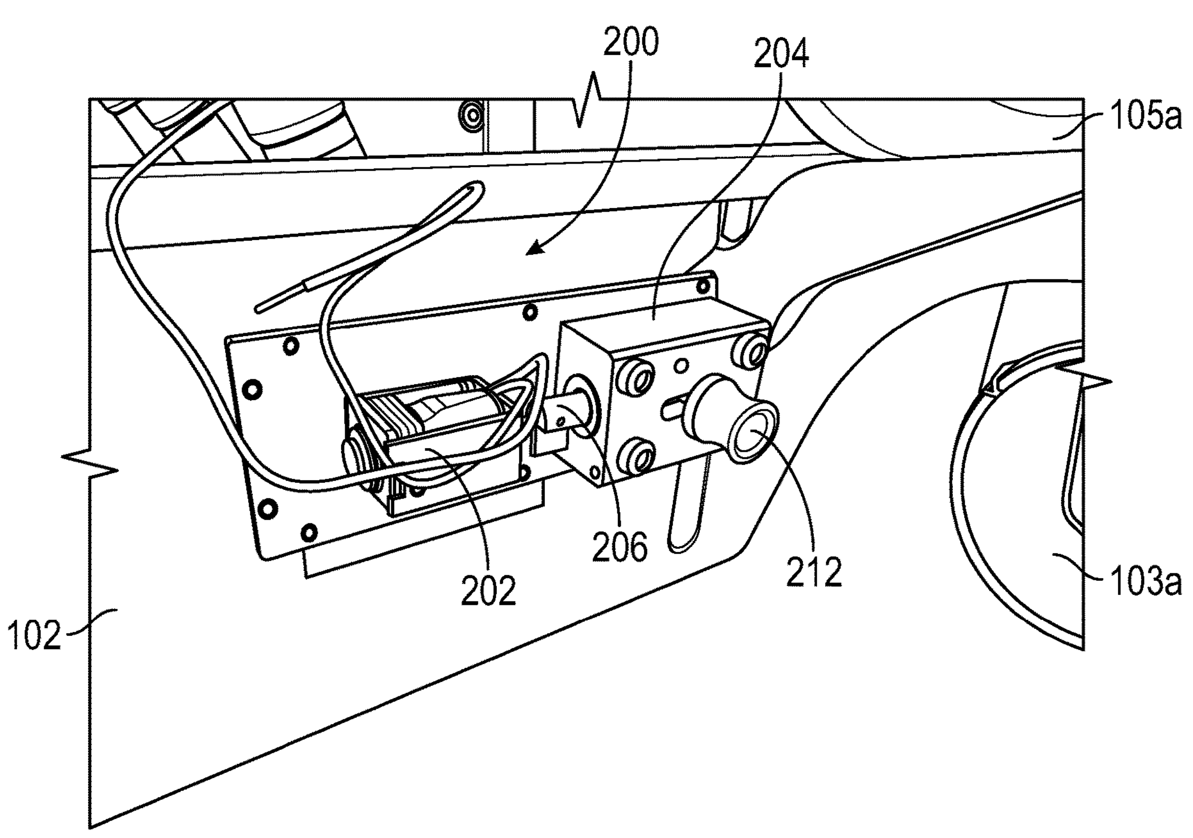

With reference to FIGS. 3-5, the first rod 112 has a first end portion **112*a* and a second end portion 112*b*. The first end portion 112*a* of the first rod 112 has the gear 116 non-rotatably fixed thereto. The second end portion 112*b* of the first rod 112 is operably coupled to the first and third casters 103*a*, 103*c*. In particular, the second end portion 112*b* of the first rod 112 has a first crank 120 and a second crank 122 fixed thereto. The first crank 120 has a first end 120*a* non-rotationally coupled to the second end portion 112*b* of the first rod 112, such that the first crank 120 rotates with the first rod 112. The first crank 120 has a second end 120*b* having a first end portion 124*a* of the first linkage 124** rotationally coupled thereto.

The first linkage 124 of the braking mechanism 110 operably couples the first rod 112 to the first caster **103*a*. The first linkage 124 is perpendicular relative to the first rod 112 and may be shorter relative to the first rod 112. Since the first end portion 124*a* of the first linkage 124 is rotationally coupled to the second end 120*b* of the first crank 120, rotation of the first crank 120 with the first rod 112 drives a movement of the first linkage 124. The first linkage 124 has a second end portion 124*b* rotationally coupled to a crank 126 of the first caster 103*c***.

The crank 126 of the first caster **103*a* has a first end 126*a* rotationally coupled to the second end portion 124*b* of the first linkage 124, and a second end 126*b* non-rotationally coupled to a locking bar 128 of the first caster 103*a*. The locking bar 128 of the first caster 103*a* extends through a housing 130 of the first caster 103*c* and is configured to selectively lock and unlock a wheel 132 of the first caster 103*a* and lock and unlock a swiveling of the wheel 132 of the first caster 103*c*. It is contemplated that the locking bar 128 may have a non-circular transverse cross-sectional profile, such as hexagonal or any suitable polygon. The locking bar 128 may interact with a central locking mechanism or cam (not shown) inside of the caster 103*a* to unlock and lock the wheel 132**.

In use, to unlock the first caster **103*a*, the first pedal 105*a* may be depressed to rotate the first rod 112 about its longitudinal axis in the direction indicated by arrow "A." Rotation of the first rod 112 in the first direction drives a rotation of the first crank 120 of the first rod 112, whereby the first crank 120 moves the first linkage 124 in a reciprocating/rotary type motion (e.g., translates and rotates) in a general direction toward the first rod 112 (i.e., away from the first caster 103*a*). Movement of the first linkage 124 towards the first rod 112 drives a rotation of the crank 126 of the first caster 103*a* and, in turn, the locking bar 128 of the first caster 103*a* in the first direction, to unlock the first caster 103*a***.

To lock the first caster **103*a*, the second pedal 105*b* may be depressed to rotate the second rod 114 about its longitudinal axis in the first direction indicated by arrow "A." Rotation of the second bar 114 in the first direction causes the first bar 112 to rotate in the opposing second direction indicated by arrow "B" due to the interaction of the gears 116, 118 of the corresponding first and second rods 112, 114. Rotation of the first rod 112 in the second direction drives a rotation of the first crank 120 of the first rod 112, whereby the first crank 120 moves the first linkage 124 in a general direction away from the first rod 112 in a reciprocating/rotary type motion. Movement of the first linkage 124 away from the first rod 112 drives a rotation of the crank 126 of the first caster 103*a* and, in turn, the locking bar 128 of the first caster 103*a* in the second direction, to lock the first caster 103*a***.

With continued reference to FIGS. 3-5, the second linkage 134 of the braking mechanism 110 operably couples the first rod 112 and the third caster **103*c*. More specifically, the second linkage 134 has a first end portion 134*a* rotationally coupled to the second crank 122 of the first rod 112, and a second end portion 134*b* rotationally coupled to a crank 136 of the third caster 103*c*. As such, rotation of the second crank 122 with the first rod 112 drives a reciprocating/rotary type movement of the second linkage 134. The second linkage 134, the second crank 122 of the first rod 122, and the crank 136 of the third caster 103*c* work together in a similar manner as the first linkage 124, the first crank 120 of the first rod 112, and the crank 126 of the first caster 103*a*** described above.

The crank 136 of the third caster **103*c* is non-rotationally coupled to a locking bar 138 of the third caster 103*c*. The locking bar 138 of the third caster 103*c* extends through a housing 140 of the third caster 103*c* and is configured to selectively lock and unlock a wheel 142 of the third caster 103*c* and lock and unlock a swiveling of the wheel 142 of the third caster 103*c***.

In use, to unlock the third caster **103*c*, the first pedal 105*a* may be depressed to rotate the first rod 112 about its longitudinal axis in the direction indicated by arrow "A." Rotation of the first rod 112 in the first direction drives a rotation of the second crank 122 of the first rod 112, whereby the second crank 122 moves the second linkage 134 (e.g., translates and rotates) in a general direction away from the first rod 112. Movement of the second linkage 134 away from the first rod 112 drives a rotation of the crank 136 of the third caster 103*c* and, in turn, the locking bar 138 of the first caster 103*c* in a direction configured to unlock the third caster 103*c***.

To lock the third caster **103*c*, the second pedal 105*b* may be depressed to rotate the second rod 114 about its longitudinal axis in the first direction indicated by arrow "A." Rotation of the second rod 114 in the first direction causes the first rod 114 to rotate in the opposing second direction indicated by arrow "B" due to the interaction of the gears 116, 118 of the corresponding first and second rods 112, 114. Rotation of the first rod 112 in the second direction drives a rotation of the second crank 122 of the first rod 112, whereby the second crank 122 moves the second linkage 134 in a general direction toward the first rod 112. Movement of the second linkage toward the first rod 112 drives a rotation of the crank 136 of the third caster 103*c* and, in turn, the locking bar 138 of the third caster 103*c* in a direction configured to lock the third caster 103*c***.

With continued reference to FIGS. 2-5, the second rod 114 of the braking mechanism 110 has a first end portion **114*a* and a second end portion 114*b*. The first end portion 114*a* of the second rod 114 has the gear 118 non-rotatably fixed thereto. The second end portion 114*b* of the second rod 114 is operably coupled to the second and fourth casters 103*b*, 103*d*. In particular, the second end portion 114*b* of the second rod 114 has a first crank 144 and a second crank 146 fixed thereto. The first crank 144 of the second rod 114 has a first end 144***a* non-rotationally coupled to the second end portion 114*b* of the second rod 114, such that the first crank 144 rotates with the second rod 114. The first crank 144 has a second end 144*b* having a first end portion 148*a* of the first arm 148 rotationally coupled thereto.

The first arm 148 of the braking mechanism 110 operably couples the second rod 114 to the second caster 103*b*. The first arm 148 is perpendicular relative to the second rod 114 and may be shorter relative to the second rod 114. Since the first arm 148 is rotationally coupled to the first crank 144, rotation of the first crank 144 with the second rod 114 drives a movement of the first arm 148. The first arm 148 has a second end portion 148*b* rotationally coupled to a crank 150 of the second caster 103*b*.

The crank 150 of the second caster 103*b* has a first end 150*a* rotationally coupled to the second end portion 148*b* of the first arm 148, and a second end 150*b* non-rotationally coupled to a locking bar 152 of the second caster 103*b*. The locking bar 152 of the second caster 103*b* extends through a housing 154 of the second caster 103*b* and is configured to selectively lock and unlock a wheel 156 of the second caster 103*b* and lock and unlock a swiveling of the wheel 156 of the second caster 103*b*.

In use, to unlock the second caster 103*b*, the first pedal 105*a* may be depressed to rotate the first rod 112 about its longitudinal axis in the direction indicated by arrow "A." Rotation of the first rod 112 in the first direction drives a rotation of the second rod 114 in the opposing second direction, as indicated by arrow "B." The first crank 144 of the second rod 114 rotates with the second rod 114, whereby the first crank 144 moves the first arm 148 (e.g., translates and rotates) in a general direction away from the second rod 114. Movement of the first arm 148 away from the second rod 114 drives a rotation of the crank 150 of the second caster 103*b* and, in turn, the locking bar 152 of the second caster 103*b* in a direction configured to unlock the second caster 103*b*.

To lock the second caster 103*b*, the second pedal 105*b* may be depressed to rotate the second rod 114 about its longitudinal axis in the first direction indicated by arrow "A." Rotation of the second rod 114 in the first direction drives a rotation of the first crank 144 of the second rod 114, whereby the first crank 144 moves the first arm 148 in a general direction toward the second rod 114. Movement of the first arm 148 toward the second rod 114 drives a rotation of the crank 150 of the second caster 103*b* and, in turn, the locking bar 152 of the second caster 103*b* in a direction configured to lock the second caster 103*b*.

The second arm 160 of the braking mechanism 110 operably couples the second rod 114 and the fourth caster 103*d*. More specifically, the second arm 160 has a first end portion 160*a* rotationally coupled to the second crank 146 of the second rod 114, and a second end portion 160*b* rotationally coupled to a crank 162 of the fourth caster 103*d*. As such, rotation of the second crank 146 with the second rod 114 drives a movement of the second arm 160. The second arm 160, the second crank 146 of the second rod 114, and the crank 162 of the fourth caster 103*d* work together in a similar manner as the first arm 148, the first crank 144 of the second rod 114, and the crank 150 of the second caster 103*b* described above.

The crank 162 of the fourth caster 103*d* is non-rotationally coupled to a locking bar 164 of the fourth caster 103*d*. The locking bar 164 of the fourth caster 103*d* extends through a housing 166 of the fourth caster 103*d* and is configured to selectively lock and unlock a wheel 168 of the fourth caster 103*d* and lock and unlock a swiveling of the wheel 168 of the fourth caster 103*d*.

In use, to unlock the fourth caster 103*d*, the first pedal 105*a* may be depressed to rotate the first rod 112 about its longitudinal axis in the direction indicated by arrow "A." Rotation of the first rod 112 in the first direction drives a rotation of the second rod 114 in the opposing second direction, as indicated by arrow "B." The second crank 146 of the second rod 114 rotates with the second rod 114, whereby the second crank 146 moves the second arm 160 (e.g., translates and rotates) in a general direction toward the second rod 114. Movement of the second arm 160 toward the second rod 114 drives a rotation of the crank 162 of the fourth caster 103 and, in turn, the locking bar 164 of the fourth caster 103*d* in a direction configured to unlock the fourth caster 103*d*.

To lock the fourth caster 103*d*, the second pedal 105*d* may be depressed to rotate the second rod 114 about its longitudinal axis in the first direction indicated by arrow "A." Rotation of the second bar 114 in the first direction drives a rotation of the second crank 146 of the second rod 114, whereby the second crank 146 moves the second arm 160 in a general direction away from the second rod 114. Movement of the second arm 160 away from the second rod 114 drives a rotation of the crank 162 of the fourth caster 103*d* and, in turn, the locking bar 164 of the fourth caster 103*d* in a direction configured to lock the fourth caster 103*d*.

As can be appreciated from the above, the braking mechanism 110 provides for a simultaneous or near simultaneous unlocking of all the casters 103*a-d* via actuation of the first pedal 105*a*, and a simultaneous or near simultaneous locking of all the casters 103*a-d* via actuation of the second pedal 105*b*. In embodiments, the braking mechanism 110 may be configured so that a depression or lifting of the first pedal 105*a* may result in a locking or unlocking of the casters 103*a-d*, or a depression or lifting of the second pedal 105*b* may result in a locking or unlocking of the casters 103*a-d*.

Figure 8:
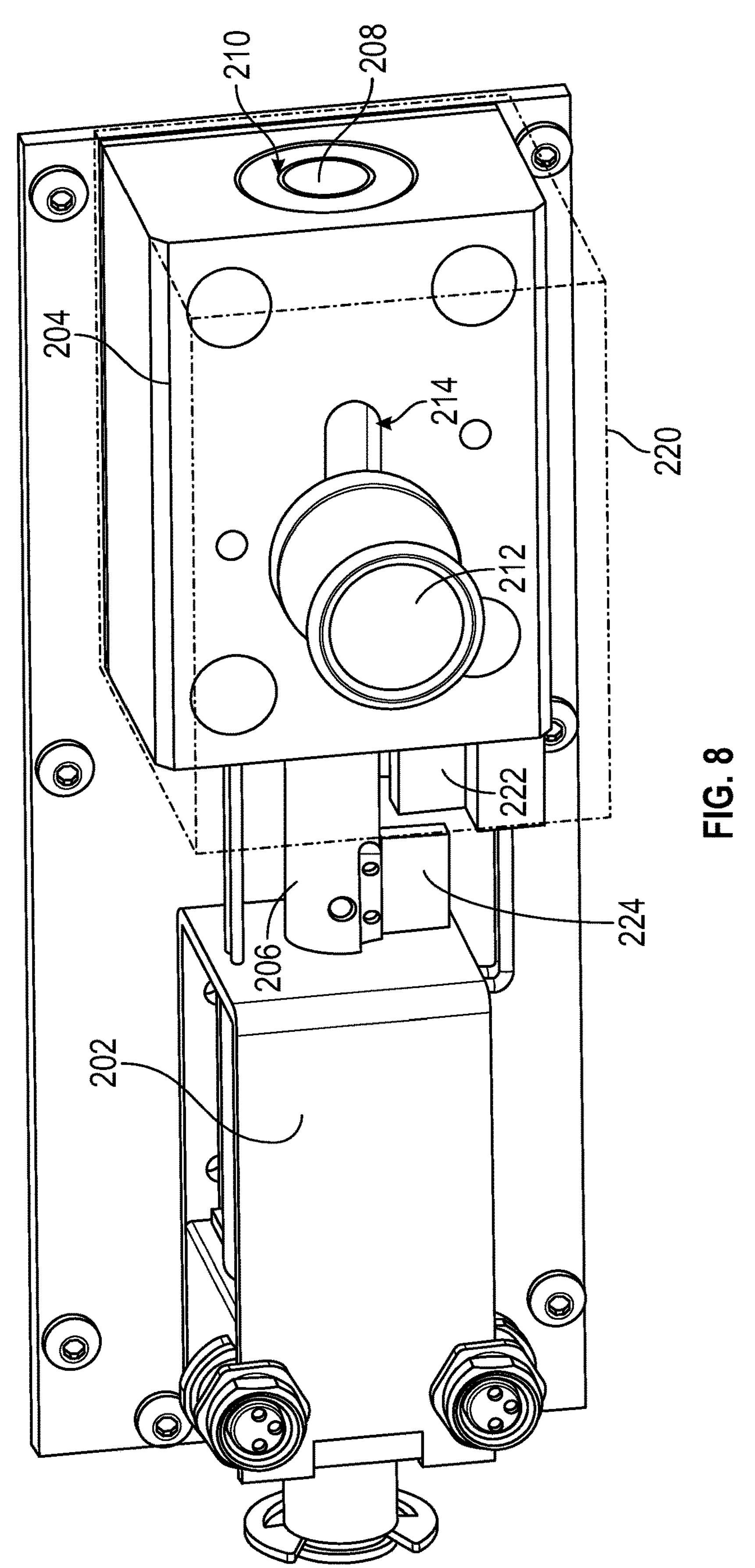
FIG. 8 is a front, perspective view of the secondary braking mechanism of FIG. 7 shown in isolation.

With reference to FIG. 8, the braking mechanism 110 may further include a sensing assembly 170 for determining whether the casters 103*a-d* are in a locked or an unlocked condition. The sensing assembly 170 includes a sensing element 172, such as, for example, a hall effect sensor, and a sensed element 174, such as, for example, a magnet. In embodiments, the sensing assembly 170 may include any suitable position sensors, such as, for example, a potentiometer, a proximity sensor, a rotary encoder, a linear variable differential transformer, an eddy-current sensor, or the like. The sensing element 172 is fixed to the base 102 (FIG. 3) of the cart 100 with a first flange 176, and the sensed element 174 is coupled to the first rod 112 with a second flange 178. The second flange 178 is non-rotationally coupled to the first rod 112, such that the second flange 178, along with the sensed element 174, rotates with the first rod 112. It is contemplated that the sensed element 174 may be attached to any suitable components of the braking mechanism 110, such as, for example, the second rod 114, the first or second linkages 124, 134, or the first or second arms 148, 160.

The sensed element 174 and the sensing element 172 are disposed adjacent one another and move in and out of alignment during a locking and unlocking of the braking mechanism 110. For example, in use, upon depressing the first pedal 105*a* (FIG. 3) to unlock the braking mechanism 110, the first rod 112 is rotated in the first direction, thereby rotating the second flange 178 of the sensing assembly 170 therewith. Rotation of the second flange 178 moves the sensed element 174 from a first position, in which the sensed element 174 is out of alignment with the sensing element 172, as shown in FIG. 8, to a second position, in which the sensed element 174 is aligned with the sensing element 172. When the sensed element 174 is in the second position, the sensing element 172 transmits a corresponding signal to the control device 4 (FIG. 1), which uses the signal to determine that the casters 103*a-d* are in an unlocked state. In embodiments, the cart 100 may be provided with an audio or visual indicator that the casters 103*a-d* are in an unlocked state.

Upon depressing the second pedal 105*b* to lock the braking mechanism 110, the second rod 114 is rotated in the first direction, which drives a rotation of the first rod 112 in the second direction, as described above. The second flange 178 of the sensing assembly 170 rotates with the second rod 114 in the second direction. Rotation of the second flange 178 moves the sensed element 174 relative to the sensing element 172 from the second position to the first position. When the sensed element 174 is in the first position, the sensing element 172 transmits a corresponding signal to the control device 4 (FIG. 1), which uses the signal to determine that the casters 103*a-d* are in a locked state.

FIGS. 7-10 illustrate a secondary braking mechanism 200 of the surgical cart 100 of FIG. 2, which is configured to prevent an inadvertent or accidental unlocking of the casters 103*a*, 103*b*, 103*c*, or 103*d* when the surgical instrument 10 (FIG. 1) is located within a patient. When a sensor, such as, for example, a sensor 13 (FIG. 1) of the surgical robotic arm 2 or the surgical cart 100 determines that the surgical instrument 10 is detached from the surgical robotic arm 2 or at least positioned outside of a patient, the secondary breaking mechanism 200 is automatically actuated, via the control device 4, to then allow for the manual actuation of the foot pedal 105*a* to unlock the casters 103*a*, 103*b*, 103*c*, or 103*d*. The secondary braking mechanism 200 also provides for a manual override in an emergency situation (e.g., power loss) to allow for the manual actuation of the secondary braking mechanism 200.

Figure 9A:
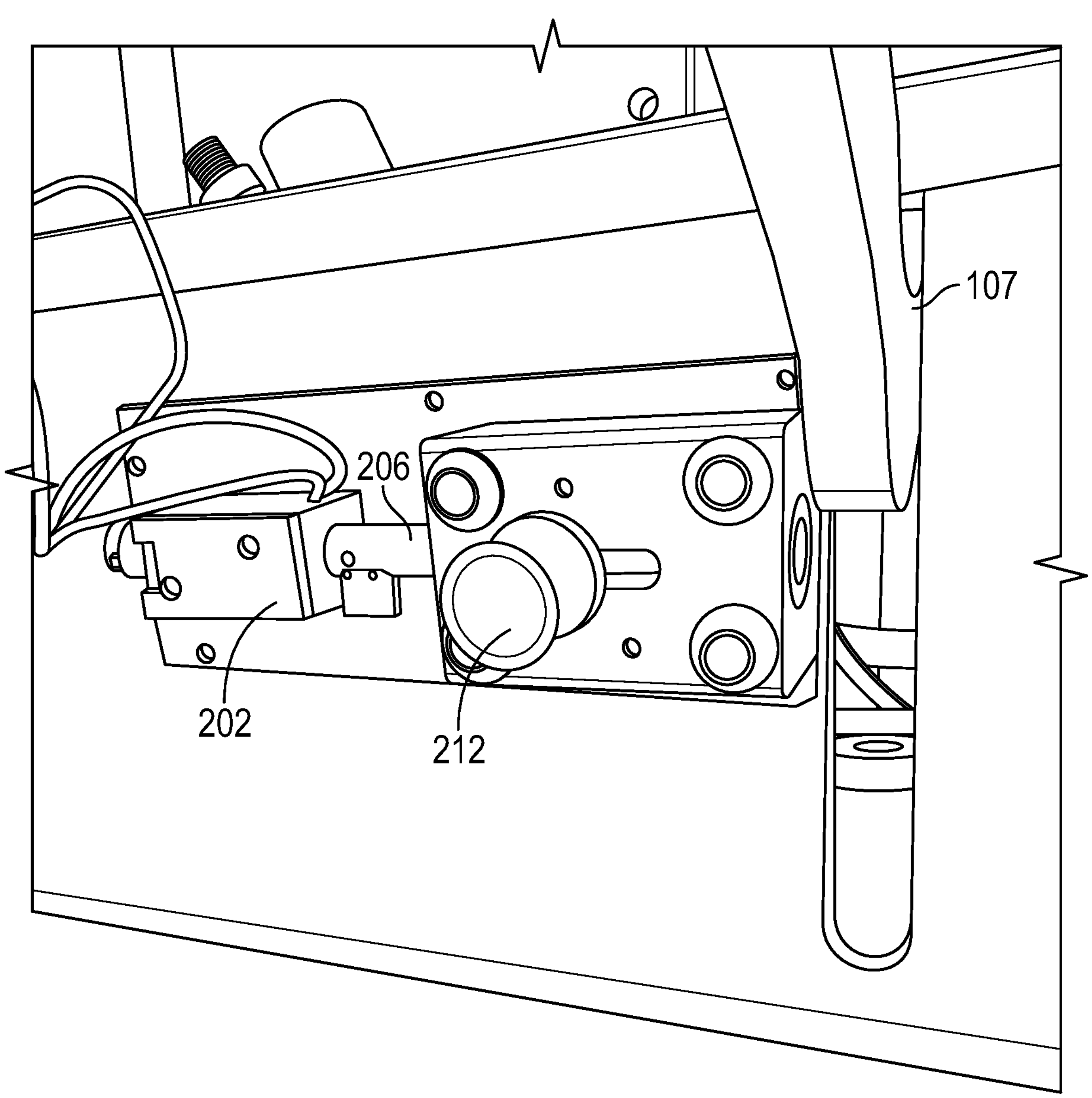
FIG. 9A is a perspective view illustrating the secondary braking mechanism in an unlocked state while a foot pedal of the surgical cart is in a braked state.
Figure 9B:
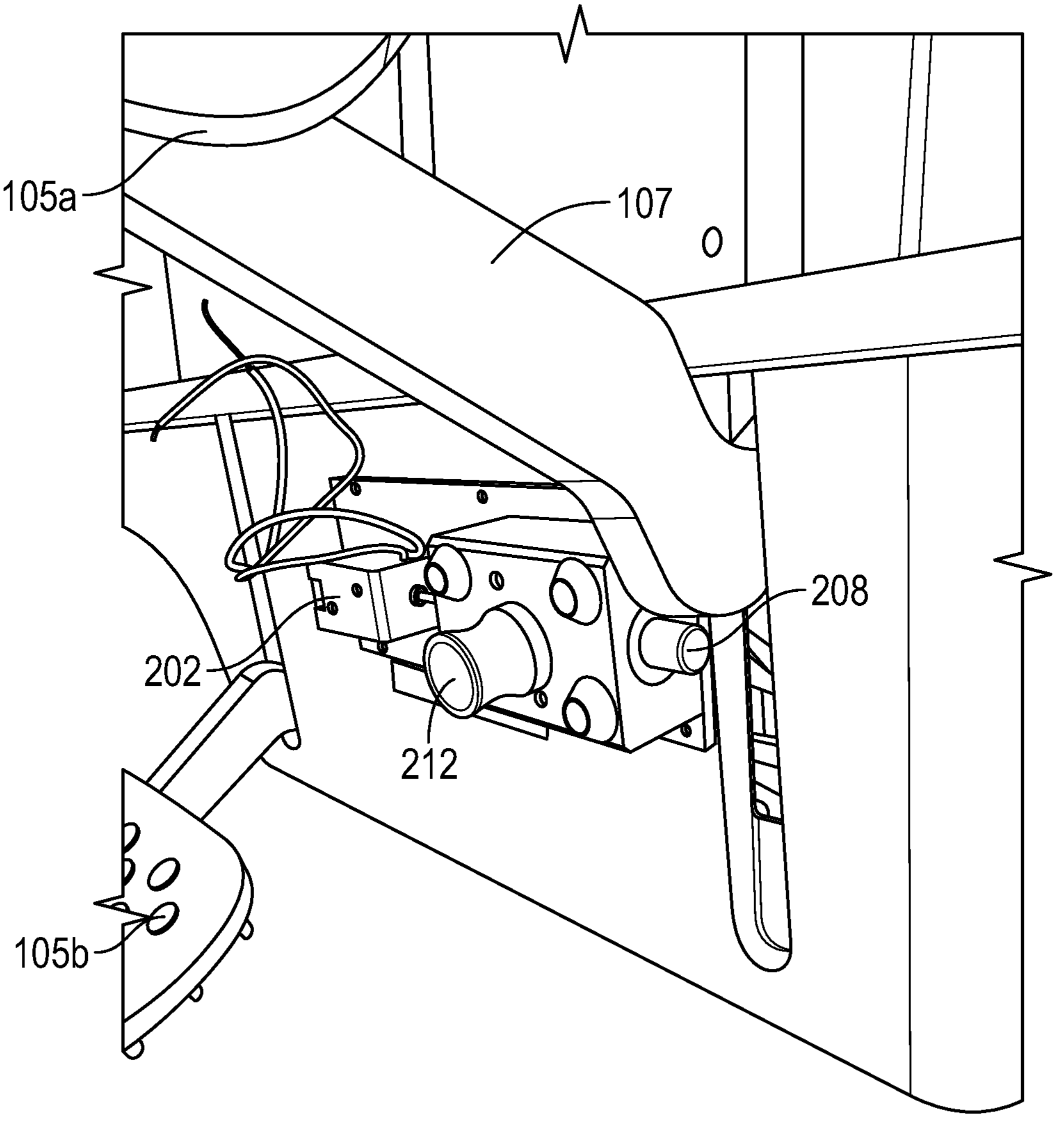
FIG. 9B is a perspective view illustrating the secondary braking mechanism in a locked state while the foot pedal is in the braked state.
Figure 10:
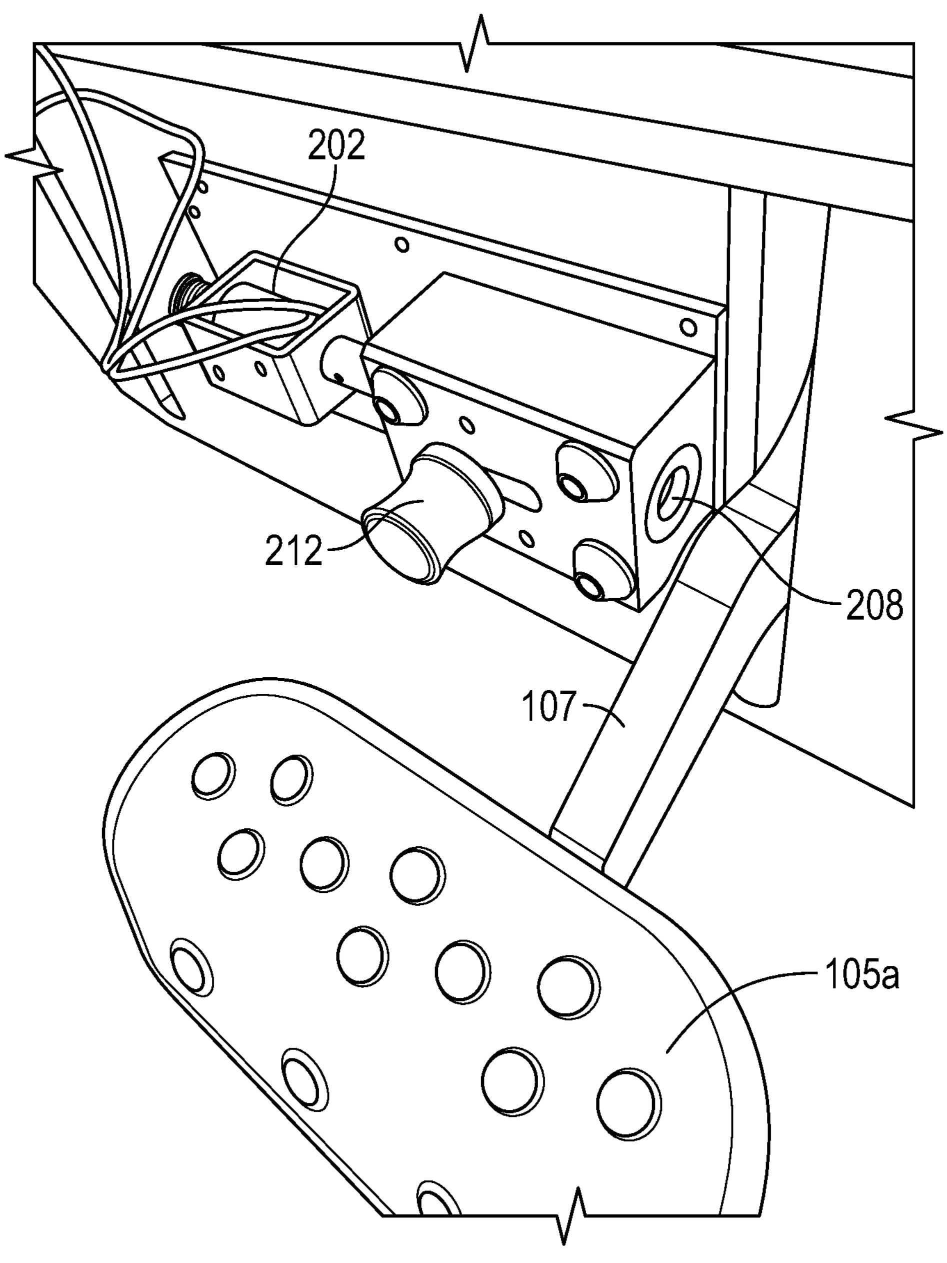
FIG. 10 is a side, perspective view illustrating the secondary braking mechanism in an unlocked state while the foot pedal is in an unbraked state.

The secondary braking mechanism 200 is attached to the base 102 of the surgical cart 100 and includes a latching solenoid 202, such as, for example, a bistable linear solenoid, and a housing structure 204 disposed adjacent the latching solenoid 202. The latching solenoid 202 has a plunger 206 or armature extending therefrom and is movable between a first or retracted position (FIG. 9A) and a second or extended position (FIG. 9B). The plunger 206 has an end 208 or pin slidably disposed within the housing structure 204 and configured to protrude through an opening 210 defined in a lateral side of the housing structure 204. The housing structure 204 is disposed adjacent an arm 107 (FIGS. 9A-9B) of the foot pedal 105*a* such that the pin 208 blocks an actuation of the foot pedal 105*a* when the plunger 206 is in the extended position, and allows for an actuation of the foot pedal 105*a* when the plunger 206 is in the retracted position.

The secondary braking mechanism 200 may further include a manual control knob 212 attached to a portion of the plunger 206 disposed within the housing structure 204. The knob 212 extends out of the housing structure 204 via a linear slot 214 defined in the housing structure 204 such that the plunger 206 is manually slidable from the second position to the first position along the slot 214. In aspects, the secondary braking mechanism 200 may further include a cover 220 (FIG. 8) detachably coupled to the base 102 and configured to conceal the manual control knob 212 and the housing structure 204 therein. The cover 220 may be detachably coupled to the base 102 via any suitable detachable fastening engagement, such as, for example, adhesive, snap-fit engagement, hook and loop fastener, a clip, etc. In this way, prior to manually moving the knob 220 to move the plunger 206 to the retracted state, a clinician must first take the affirmative step of removing the protective cover 220.

The secondary braking mechanism 200 may further include a sensor assembly, such as, for example, an optical sensor 222 and a sensor flag 224 (FIG. 8). The optical sensor 222 may be fixed relative to the base 102 of the surgical cart 100 and the sensor flag 224 may be fixed to the plunger 206 such that the sensor flag 224 moves with the plunger 206 as the plunger 206 moves between the retracted and extended positions. The optical sensor 222 may be in communication with the control device 4 to communicate to the control device 4 whether the plunger 206 is in the extended position. The control device 4 may be or may include a processor in communication with the latching solenoid 202, via a wired or wireless connection, and is configured to cause the plunger 206 to move between the retracted and extended positions.

In operation, the surgical cart 100 may be moved to a desired location within a operation room "OR" via the casters 103*a*, 103*b*, 103*c*, 103*d*. Upon positioning the surgical cart 100 in the desired location, the foot pedal 105*b* (FIG. 3) may be actuated to transition the casters 103*a*, 103*b*, 103*c*, 103*d* from the unlocked state to the locked state via the mechanical linkages described in detail above with reference to FIGS. 2-6. Upon actuating the foot pedal 105*b*, the sensing assembly 170 (FIG. 8) communicates to the control device 4 that the casters 103*a*, 103*b*, 103*c*, 103*d* are in a locked state. Prior to attaching a surgical instrument 10 to the surgical robotic arm 2, the foot pedal 105*a* may be actuated to unlock the casters 103*a*, 103*b*, 103*c*, 103*d* to allow for a repositioning of the surgical cart 100 as desired by the clinician.

Upon the surgical instrument 10 being attached to the surgical robotic arm 2 and while the foot pedal 105*b* is in an actuated (locked) state as determined by the sensing assembly 170 (FIG. 8), the control device 4 (FIG. 1), as programmed, actuates the latching solenoid 202, whereby the latching solenoid 202 moves the end 208 of the plunger 206 from the retracted position (FIG. 9A) to the extended position (FIG. 9B). In the extended position, the end 208 of the plunger 206 prevents the brake pedal 105*a* from moving from the second position (FIG. 9B) to the first position (FIG. 10A). As such, an inadvertent or intentional attempt at unlocking the casters 103*a*, 103*b*, 103*c*, 103*d* of the surgical cart 100 is thwarted by the plunger 206 so long as the surgical instrument 10 remains attached to the surgical robotic arm 2. In aspects, the control device or processor 4 may be configured to actuate the latching solenoid 202 to move the plunger 206 to the extended position upon the surgical instrument 10 being moved to a location within a patient or to a predetermined unsafe distance from the patient.

To actuate the secondary braking mechanism 200 to enable movement of the surgical cart 100, the surgical instrument 10 is detached from the surgical robotic arm 2. In aspects, to actuate the secondary braking mechanism 200 to enable movement of the surgical cart 100, the surgical instrument 10 may remain attached to the surgical robotic arm 2, but is moved out of the patient or to a predetermined safe distance from the patient. It is contemplated that a camera may be provided for determining the distance between the surgical instrument 10 and the patient. In aspects, the secondary braking mechanism 200 may be actuated upon the surgical robotic arm 2 moving to its extended state.

Upon detaching the surgical instrument 10 from the surgical robotic arm 2 or moving the surgical instrument 10 out of the patient, the control device 4, as programmed, actuates the latching solenoid 202 to move the plunger 206 from the extended position to the retracted position. With the pin 208 of the plunger 206 out of a blocking position with the arm 107 of the foot pedal 105*a*, the clinician may actuate or depress the foot pedal 105*a* to unlock the casters 103*a*, 103*b*, 103*c*, 103*d*.

In an emergency situation, such as, for example, during a power loss, the detachment of the surgical instrument 10 from the surgical robotic arm 2 may fail to actuate the latching solenoid 202. Therefore, to unlock the casters 103*a*, 103*b*, 103*c*, 103*d* in this situation, the clinician detaches the cover 220 of the secondary braking mechanism 200 to gain access to the knob 212 and then slides the knob 212 to manually retract the plunger 206. With the plunger 206 held in the retracted position, the clinician or another clinician may depress the foot pedal 105*a* to unlock the casters 103*a*, 103*b*, 103*c*, 103*d*.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A surgical cart for supporting a robotic arm, comprising:
- a base;
- at least one caster coupled to the base;
- a brake pedal operably coupled to the base and configured to move between a pedal first position, in which the at least one caster is free to roll, and a pedal second position, in which the at least one caster is prevented from rolling;
- a latching solenoid coupled to the base adjacent the brake pedal, the latching solenoid having a plunger configured to move between a plunger first position, in which the brake pedal is free to move between the pedal first and second positions, and a plunger second position, in which the brake pedal is prevented from moving from the pedal second position to the pedal first position; and
- a sensor system coupled to the base, the sensor system configured to determine a distance between a surgical instrument supported by the robotic arm and a patient,
- wherein the latching solenoid is in communication with the sensor system and is configured to maintain the plunger in the plunger second position to prevent the brake pedal from moving from the pedal second position to the pedal first position until the distance is at least a predetermined safe distance.

2. The surgical cart according to claim 1, wherein the latching solenoid is configured to automatically move the plunger from the plunger first position to the plunger second position in response to the brake pedal moving to the pedal second position.

3. The surgical cart according to claim 2, wherein the latching solenoid is configured to automatically move the plunger from the plunger second position to the plunger first position upon receiving a communication that a surgical instrument is detached from the surgical robotic arm or a surgical instrument is removed from a patient.

4. The surgical cart according to claim 1, further comprising a processor in communication with the latching solenoid and configured to cause the plunger to move between the plunger first and second positions.

5. The surgical cart according to claim 1, wherein the latching solenoid is configured to automatically move the plunger from the plunger first position to the plunger second position upon both of the following occurring:
- the brake pedal is moved to the pedal second position; and
- the latching solenoid receives a communication that a surgical instrument is attached to the robotic arm or a surgical instrument is within a patient.

6. The surgical cart according to claim 1, further comprising a manual control knob attached to the plunger such that the plunger is manually movable from the plunger second position to the plunger first position.

7. The surgical cart according to claim 6, further comprising a cover detachably coupled to the base and configured to conceal the manual control knob.

8. The surgical cart according to claim 1, wherein the sensor system comprises a camera.

9. A surgical robotic assembly, comprising:
- a surgical robotic arm configured to support a surgical instrument;
- a processor in communication with the surgical robotic arm; and
- a surgical cart including:
  - cart base;
  - a support column extending vertically from the cart base and configured to support the surgical robotic arm;
  - at least one caster coupled to the base;
  - a brake pedal operably coupled to the base and configured to move between a pedal first position, in which the at least one caster is unlocked, and a pedal second position, in which the at least one caster is locked;
  - a latching solenoid coupled to the base adjacent the brake pedal and in communication with the processor, wherein the latching solenoid, in response to a command from the processor, is configured to move a plunger between a plunger first position, in which the plunger does not prevent the brake pedal from moving from the pedal second position to the pedal first position, and a plunger second position, in which the plunger prevents the brake pedal from moving from the pedal second position to the pedal first position; and
  - a sensor system coupled to the surgical cart, the sensor system in communication with the processor and configured to determine a distance between the surgical instrument and a patient,
  - wherein the processor is configured to inhibit commanding the latching solenoid to move the plunger from the plunger second position to the plunger first position unless the distance is at least a predetermined safe distance.

10. The surgical robotic assembly according to claim 9, wherein the surgical cart further includes a sensor assembly configured to determine whether the brake pedal is in the pedal first or pedal second positions.

11. The surgical robotic assembly according to claim 10, wherein the sensor assembly is configured to communicate to the processor the position of the brake pedal.

12. The surgical robotic assembly according to claim 11, wherein the surgical robotic arm includes a sensor configured to determine whether the surgical instrument is attached thereto or whether the surgical instrument is within a patient, and the processor is configured to move the plunger from the plunger first position to the plunger second position upon both of the following occurring:

the brake pedal is moved to the pedal second position; and the sensor of the surgical robotic arm determines that the surgical instrument is attached to the surgical robotic arm or the surgical instrument is within a patient.

13. The surgical robotic assembly according to claim 12, wherein the processor is configured to cause the latching solenoid to move the plunger from the plunger second position to the plunger first position upon receiving a communication from the sensor of the surgical robotic arm that the surgical instrument is detached from the surgical robotic arm or the surgical instrument is removed from the patient.

14. The surgical robotic assembly according to claim 9, wherein the sensor system comprises a camera.

15. A surgical cart for supporting a robotic arm, comprising:

a base;

at least one caster coupled to the base;

a brake pedal operably coupled to the at least one caster and configured to move between a pedal first position, in which the at least one caster is unlocked, and a pedal second position, in which the at least one caster is locked;

a latching solenoid coupled to the base, wherein the latching solenoid is configured to move a plunger between a plunger first position, in which the plunger does not prevent the brake pedal from moving from the pedal second position to the pedal first position, and a plunger second position, in which the plunger prevents the brake pedal from moving from the pedal second position to the pedal first position, wherein the plunger includes a pin configured to protrude through an opening of a housing structure disposed adjacent an arm of the brake pedal such that the pin blocks actuation of the brake pedal when the plunger is in the plunger second position;

a manual control knob attached to the plunger such that the plunger is manually movable from the plunger second position to the plunger first position, wherein the manual control knob extends out of the housing structure such that the pin of the plunger is manually actuatable; and a cover detachably coupled to the base and configured to conceal the manual control knob, wherein the cover is configured such that, prior to manually actuating the manual control knob to move the plunger to the first plunger position, a clinician must remove the cover to access the manual control knob, the manual control knob providing a manual override in an emergency situation comprising a power loss.

16. The surgical cart according to claim 15, wherein the latching solenoid is configured to automatically move the plunger from the plunger first position to the plunger second position in response to the brake pedal moving to the pedal second position.

17. The surgical cart according to claim 16, wherein the latching solenoid is configured to automatically move the plunger from the plunger second position to the plunger first position upon receiving a communication that a surgical instrument is detached from the surgical robotic arm or a surgical instrument is removed from a patient.

18. The surgical cart according to claim 15, further comprising a processor in communication with the latching solenoid and configured to cause the latching solenoid to move between the plunger first and plunger second positions.

19. The surgical cart according to claim 15, wherein the latching solenoid is configured to automatically move the plunger from the plunger first position to the plunger second position upon both of the following occurring:

the brake pedal is moved to the pedal second position; and the latching solenoid receives a communication that a surgical instrument is attached to the surgical robotic arm or a surgical instrument is within a patient.

20. The surgical cart according to claim 15, further comprising a plunger-position sensing assembly including an optical sensor fixed relative to the base and a sensor flag fixed to the plunger such that the sensor flag moves with the plunger, the optical sensor configured to generate a signal indicative of whether the plunger is in the plunger second position.

* * * * *